United States Patent [19]

Nakano et al.

[11] 4,332,897
[45] Jun. 1, 1982

[54] NOVEL BACTERIOPHAGE AND METHOD FOR PREPARING SAME

[75] Inventors: Eiichi Nakano, Saitama; Narimasa Saito, Noda; Danji Fukushima, Omiya, all of Japan

[73] Assignee: Noda Institute for Scientific Research, Noda, Japan

[21] Appl. No.: 895,602

[22] Filed: Apr. 12, 1978

[30] Foreign Application Priority Data

Apr. 26, 1977 [JP] Japan .................................. 52/47409

[51] Int. Cl.$^3$ ............................................ C12N 15/00
[52] U.S. Cl. .................................... 435/172; 435/238; 435/253; 435/235; 435/317
[58] Field of Search ............... 435/235, 236, 172, 253, 435/238, 317

[56] References Cited

U.S. PATENT DOCUMENTS 4,259,444  3/1981  Chakrabarty .

OTHER PUBLICATIONS

Book: Author—Pelczar et al.; Title—*Microbiology*, Fourth Edition, McGraw-Hill Book Company; pp. 228–232.
Aritcle: Author—Kokisato et al.; Title—*Suppressor–Sensitive Mutants of Coliphage* $\phi 80$, Virology 34, (1968), pp. 637–649.
Rambach et al., Proc. Natl. Acad. Sci USA vol. 74 pp. 3927–3930 (Oct. 1974).
Lamanna et al., Basic Bacteriology, It's Biological and Chemical Background, 3rd Ed. pp. 723–727 (1965).
Metzler, Biochemistry, The Chemical Reactions of Living Cells, Academic Press Inc. pp. 945–946 (1977).
Scott et al., Molecular Cloning of Recombinant DNA pp. 133–153 (1977).
Lewin, Gene Expression-3 pp. 269, 270, 879, 886–901 (1977).
Murray et al., Nature vol. 251 pp. 476–481 Oct. 11, 1974.

*Primary Examiner*—Alvin E. Tanenholtz
*Attorney, Agent, or Firm*—Schuyler, Banner, Birch, McKie & Beckett

[57] ABSTRACT

A novel bacteriophage whose DNA molecule has endonuclease-sensitivity only in the DNA region carrying genetic information for the production of phage coat proteins can be obtained by isolating an endonuclease-resistant mutant from one of the lambdoid bacteriophages and mating the resulting bacteriophage with a lambdoid phage having endonuclease-sensitivity in the DNA region carrying genetic information for the production of coat proteins.

17 Claims, No Drawings

NOVEL BACTERIOPHAGE AND METHOD FOR PREPARING SAME

This invention relates to a novel bacteriophage and a method for preparing same.

The genetic manipulation is a new research field initiated as the result of timely union between, on the one hand, the rapid progress in the researches on genetic and chemical properties of replicons such as plasmids and bacteriophages and, on the other hand, the progress in the researches on enzymes associated with DNA (deoxyribonucleic acid), especially endonucleases which recognize the specific sequences of nucleotides in DNA and cause cleavage of polynucleotide chains (restriction enzyme) and DNA-ligases.

The research on genetic manipulation is believed to lead the biology to a new and profound domain where it has never been reached with conventional scientific techniques. Above all, anticipated emancipation of the gene system from its dependence on natural recombination is a problem which has attracted a keen interest. Further, it is expected that such a manipulation, if fully worked out, will create microorganisms having "desirable characters" and in some future will be able to harness higher organisms to serve the human society.

Various procedures have heretofore been proposed for the gene recombination. As an example, there is a known procedure for the in vitro recombination of Drosophila melanogaster DNA with λ (lambda) phage DNA. However, since the site of recombination is the DNA region carrying the genetic information necessary for lysogenization of the phage, it is impossible to integrate the resulting hybrid DNA into the host DNA. Consequently, in the practical case it is necessary to preserve always the host cell and the phage for ready use, but the preservation of the phage presents a problem. In addition, when a plasmid having a recombined genetic information for a specific enzyme protein infected the host, production of the specific enzyme would take place continuously (owing to the gene dosage effect) even when the host cells are in preserved state, thus causing considerable disturbance in host metabolism and inducing various secondary variations to compensate the disturbance. For instance, some of the plasmids undergo variation to decrease the number of copies of the plasmid, others acquire through variation the behavior to decrease the function or synthetic activity of the enzyme or to affect other metabolic systems so as to correct the distorted character. In actual cases, because of such secondary variations which profoundly affect the results, the genetic recombination procedure is far from being satisfactory.

Under the circumstances, the present inventors conducted an extensive investigation using bacteriophage in order to eliminate the aforementioned difficulties.

The phage particle generally consists of protein and nucleic acid (DNA or RNA) forming a structure in which the nucleic acid is surrounded by the protein (called coat proteins). The nucleic acid bears in memory all of the genetic information necessary for the bacteriophage to multiply on infecting a host cell. In the case of the bacteriophage λ for example, the one half of the DNA chain carries genes which are necessary for self replication and the other half carries the genetic information for the synthesis of coat proteins (A. D. Hershey, editor, "The Bacteriophage Lambda," published by Cold Spring Harbor Lab., p. 45 1971). Accordingly, if a phage DNA segment carrying the genetic information coding for the synthesis of coat proteins is replaced by another DNA segment carrying the genetic information coding, for example, for the synthesis of a useful enzyme by the aid of endonuclease and DNA ligase, it seems possible to induce the phage, on infecting a host cell, to synthesize a large amount of the useful enzyme in place of the coat protein.

However, since bacteriophage generally has endonuclease-sensitivity even in its DNA region participating in self-replication, it undergoes scission (cleavage) in said region by the action of endonuclease, and the self-replication becomes impossible.

Therefore, the present inventors concentrated their efforts to eliminate the endonuclease-sensitivity of the DNA region participating in self-replication without impairing the self-replicating ability and to retain the endonuclease-sensitivity of the DNA region participating in the synthesis (production) of coat proteins. As the result, it was found that by the hybridization between a phage containing none of the sites susceptible to cleaving by endonuclease and a phage of the same or related species having a cleavage sites in the intended DNA region or related region it is possible to prepare easily and efficiently a self-reproducible hybrid DNA molecule which retains endonuclease-sensitivity in the intended DNA region and is self-reproducible in cloning of gene in genetic manipulation. Based on this finding, the present invention has been accomplished.

An object of this invention is to provide a novel and useful bacteriophage composed of the DNA molecule sensitive to an endonuclease only in the region where the genetic information for the production of coat proteins is located and therefore capable of replacing the genetic information of said region by another intended genetic information to produce a self-reproducible hybrid DNA molecule and to provide a method for preparing said novel bacteriophage.

Other objects and advantages of the present invention will become apparent from the following description.

Thus, the bacteriophage of this invention is that composed of the DNA molecule made endonuclease-sensitive only in the DNA region carrying genetic information for the production of coat proteins. According to this invention, a bacteriophage composed of the phage DNA molecule made sensitive to an endonuclease only in the genetic information region responsible for the production of coat proteins can be obtained by making a bacteriophage of the lambdoid phage species endonuclease-resistant and mating the resulting bacteriophage with a lambdoid phage having endonuclease-sensitivity in the DNA region responsible for the production of coat proteins.

The invention is described below in detail.

Although bacteriophage generally multiplies depending more or less on the function of its host, it is a replicon capable of multiplying independently outside the host chromosome, namely, it is in the autonomous state. The bacteriophage used in this invention is a temperate phage having such property that when the phage infected a host cell, its phage DNA can be integrated in the host cell DNA under appropriate conditions (lysogeny). Preferable temperate phages are lambdoid phages including λ (IFO 20016), 434 (IFO 20018), 82 (IFO 20019), φ80 (IFO 20020), φ170 (IFO 20021), etc. Also usable are those phages lysogenized in appropriate host cell, such as, for example, φ80 lysogenized in E. coli W 3110 [E. coli K12 strain W 3110 (φ80) (ATCC 31277)], λcI 857 lysogenized in *E. coli* W 3350 [*E. coli* K12 strain W 3350 (λcI 857) (ATCC 31278)], etc. The above-mentioned two strains have been deposited in the American Type Culture Collection (ATCC) and assigned the ATCC number 31277 and 31278, respectively.

As for the preparation of an endonuclease-resistant phage, a preferred endonuclease is a high specificity endonuclease capable of recognizing specific sites in the DNA chain and cleaving the DNA double helix within the recognized sites so as to form "staggered" cohesive ends. A most suitable endonuclease is a restriction enzyme such as Eco RI, Bam HI, or Hind III. The restriction enzymes are available from Seikagaku Kogyo Co. or Boehringer Mannheim Yamanouchi.

The endonuclease-resistant phage such as, for example, a mutant phage absolutely resistant to cleavage by a restriction enzyme can be obtained, for example, in the following manner: Alternate cultivation of a lambdoid phage in a host containing a restriction enzyme and in another host containing no restriction enzyme results in extinction of a phage susceptible to the action of the restriction enzyme and continuous increase in the population of a mutant difficulty susceptible to said action. By such microbial concentration, it is possible to obtain finally a phage (restriction enzyme-resistant phage) containing DNA absolutely unsusceptible to the action of the restriction enzyme (i.e. DNA whose chain is perfectly uncleavable by the action of the restriction enzyme).

The resistant phage can also be obtained more speedily by locally deleting the region cleavable by the restriction enzyme and then using the microbial concentration technique. The method for locally eliminating the region of DNA cleavable by restriction enzyme consists in isolating a deletion mutant in which the phage DNA region including the cleavable sites has been deleted. When the sites cleavable by the restriction enzyme are located in a DNA region unnecessary for the survival of the phage, the resistance of the phage against restriction enzyme can be increased by isolating the mutant in which said region has been deleted. Owing to deletion of the DNA region including the cleavable sites, the deletion mutant has a reduced specific gravity and an improved thermal stability. By taking advantage of these properties, the mutant can be separated from an ordinary phage culture medium, for example, by cesium chloride (CsCl) density-gradient centrifugation, whereby the separation is effected by centrifugation of the culture admixed with cesium chloride, or by heating the phage culture at 60° C. and separating the survived phage. The separated mutant is subjected to microbial concentration by culturing the mutant alternately in a host having a restriction enzyme and a host having no restriction enzyme. In such a manner, a phage having DNA perfectly unsusceptible to the action of the restriction enzyme can be obtained more quickly.

In order to insert the sites cleavable by the restriction enzyme into an intended region of the resulting phage DNA, which is absolutely free from the sites cleavable by the restriction enzyme, the phage is mated with a lambdoid phage having endonuclease-sensitivity in the DNA region carrying genetic information for the production of coat proteins. The mating is carried out by addition of two phage suspensions, one resistant and the other sensitive to the restriction enzyme ($10^9$–$10^{10}$/ml, each), successively or (simultaneously) after mixing them to a suspension of *E. coli* ($10^8$–$10^9$/ml) sensitive to both phages. The mating is also possible by inducing multiplication of an endonuclease-resistant or sensitive phage lysogenized in *E. coli* strain K12 and then infecting the induced lysogen with another endonuclease-sensitive or -resistant phage. The *E. coli* cells infected with these phages as above are shaken at 37° C. for 1 to 2 hours in a medium such as, for example, Tryptone medium (any medium can be freely used so long as growth of the host cells is possible).

For the sensitive *E. coli* may be used any of the K12 strains, including, for example, W 3110 (ATCC 27325), W 3350 (ATCC 27020) and 1100 (Max Plank Institut, F. R. Germany). The *E. coli* may be used in the form of culture fluid or in the form of suspension prepared by centrifuging the culture to remove the supernatant, suspending the sediment in a 10 mM $MgCl_2$ solution, and shaking for one hour at 37° C. The latter form is better for the adsorption and infection of the phage.

In a manner as described above, it is possible to obtain about $10^5$/ml of a phage having endonuclease-sensitivity only in the DNA region carrying genetic information for the production of coat proteins.

Isolation of the intended phages from the culture thus obtained is effected in the following way.

As an example, a phage A and a phage B are selected at random from the lambdoid phage group. If the endonuclease-resistant phage A is mated with the phage B having endonuclease-sensitivity in the DNA region carrying genetic information for the production of coat proteins to create a new phage in which the DNA region for the production of coat proteins comes from the sensitive phage B and the DNA region participating in self-replication from the resistant phage A. The new phage thus obtained can multiply in a *E. coli* cells which are A-resistant and B-immune (*E. coli* cells which cannot adsorb phage A and in which phage B is lysogenized), while other phages cannot grow. Thus, it is possible to isolate the new phage.

The A-resistant and B-immune *E. coli* is obtained in the following manner.

At first, the phage A is allowed to infect the *E. coli* cells preferably under the conditions unfavorable for lysogenization. For instance, when *E. coli* cells are infected with phage A mutant particles lacking lysogeny in a proportion of 1:100, the survived cells are those resistant to the phage A. The temperate phage is generally lysogenized in *E. coli* cells at a certain probability and forms a turbid plaque, whereas the mutant lacking lysogeny forms a transparent plaque. Consequently, the phage lacking lysogeny can be obtained by collecting the phage particles in transparent plaques. It is desirable to use the phage thus collected for the operational simplification in sorting out a phage-resistant *E. coli*.

The *E. coli* thus sorted out is resistant to the phage A and does not adsorb the phage A by nature. The adsorption specificity depends entirely on the protein existing in the tail of the phage. Since the genetic information for the adsorption of the above phage is located in the DNA region participating in the production of coat proteins, a phage containing the genetic information for the production of coat proteins of the phage A cannot be adsorbed on *E. coli* cells resistant to the phage A and, hence, cannot enter these cells. Whether or not the host cells are phage-resistant mutant can be confirmed by the following way. As an example, since an *E. coli* resistant to λ phage cannot utilize maltose, it is detectable by the absence of red stain on the cell when it is cultivated in a medium containing maltose and indicators comprising methylene blue and eosine yellow.

Next, the A-resistant host is imparted with B-immunity. This can be accomplished by infecting the A-resistant host cell with a phage, such as phage B, in which the genetic information controlling the immunity is carried by the DNA region participating in self-replication, to produce a host cell in which DNA of the phage B is integrated into the host DNA. If a phage having the same immunity as that of the phage B DNA, which had been integrated into the host cell, entered this host cell, it cannot multiply therein. To ascertain whether the DNA of the phage B was integrated into the host DNA, the host cells are, for example, exposed to ultraviolet rays to induce the phage multiplication. If the phage B is liberated on shaking-culture of the irradiated host cells, integration of the phage B DNA into DNA of the host cell is ascertained.

The bacteriophage DNA having endonuclease-sensitivity only in the DNA region carrying genetic information for the production of coat proteins is susceptible to cleavage only in said region by the action of the endonuclease, thus enabling the replacement of the information for the production of coat proteins by the intended genetic information to take place easily and efficiently.

A recombinant DNA is formed by replacing the DNA sequences carrying genetic information for the production of coat proteins of the new phage DNA obtained above with the intended DNA sequences. The resulting recombinant DNA is allowed to infect the host so as to be integrated into the host DNA. The host cell thus treated (lysogen) can be stored for future use. Thus, it is unnecessary to preserve always the host cell and the recombinant phage, preservation of the latter being rather difficult. When needed, multiplication of the recombinant phage is induced to "amplify" the genetic information and the induced cells are cultured in a medium such as, for example, Tryptone medium. In such a manner, a great amount of specific protein (as much as 50% of the soluble protein of the host cell; see N. E. Murray and K. Murray, Nature vol. 251 (1974) pp. 476-481) can be produced owing to the amplified genetic information, which enable the purification of the specific protein to take place very easily and efficiently. For these reasons the new bacteriophage obtained above will contribute greatly to the industry.

The present inventors have found that when $E.$ $coli$ $trp^-$ host lysogenized with the recombinant phage constructed by introducing $E.$ $coli$ $trp$ gene into the new phage obtained as above is cultured after induction of phage multiplication, a large amount of enzyme for tryptophan biosynthesis is produced.

The invention is illustrated below with reference to Example, but the invention is not limited thereto.

EXAMPLE

Preparation of a novel phage, $\lambda cI857RI^rh80$, susceptible to cleavage by the action of a restriction enzyme, Eco RI, of $E.$ $coli$ only in the DNA region carrying the genetic information for the production of coat proteins.

1. Isolation of a deletion mutant phage $\lambda cI857b6042$ from phage $\lambda cI857$.

1-1. One platinum-loopful of $E.$ $coli$ K12 strain W 3350 ($\lambda cI857$) (ATCC 31278) was inoculated into 3 ml of Tryptone medium and cultured by shaking for 16 hours at 30° C. The resulting 3 ml preculture was mixed with 30 ml of Tryptone medium, cultured by shaking for 3 hours at 30° C., and then for 20 minutes at 43° C. to induce multiplication of $\lambda cI857$. The cultivation was continued for further 3 to 6 hours at 30° C. until bacteriolysis had taken place and the culture had become nearly transparent when the cultivation was discontinued. The culture liquor was centrifuged to remove cell fragments, the supernatant having been phage $\lambda cI857$ suspension containing about $10^{11}$/ml of phage particles.

1-2. A 0.1 ml portion of the phage $\lambda cI857$ suspension was suspended in 5 ml of Tris buffer solution (pH 8.2) containing 0.02 M ethylenediaminetetraacetic acid (EDTA), thereafter kept at 40° C. for 10 minutes and then diluted with 0.01 M Tris buffer solution (pH 7.2) containing 0.01 M $MgCl_2$ (hereinafter this solution is referred to as Tris-Mg buffer solution) to a final particle concentration of $10^7$/ml. A 0.1 ml portion of the diluted phage solution and 0.25 ml of the overnight culture of $E.$ $coli$ W 3110 (ATCC 27325) prepared by incubation at 37° C. for 16 hours in Tryptone medium were spread on a Tryptone-agar plate (see Note (1) mentioned later) together with 3 ml of molten $B_1$-soft agar (see Note (2) mentioned later) held at 46° C. and cultured at 37° C. for 4 to 5 hours. The phage on the plate was leached with 4 ml of Tris-Mg buffer solution and preserved in a rubber-stoppered sterilized small test tube. Using a portion of this phage suspension, the same procedure as described above was repeated five times.

1-3. Using the phage obtained in 1-2, the same procedure as described in 1-2 was repeated four times, except that the treatment was carried out at 60° C. for 10 minutes in place of the treatment at 40° C. for 10 minutes. The resulting phage suspension was diluted to $10^3$/ml. A 0.1 ml portion of the diluted phage suspension was mixed with 0.25 ml of the aforementioned culture of $E.$ $coli$ W 3110, then spread on Tryptone-agar plate together with $B_1$-soft agar and cultured overnight at 37° C. The phage particles in one of the about 100 plaques on the plate were picked up with a bamboo spit and suspended in Tris-Mg buffer solution to obtain phage strain $\lambda cI857b6042$.

The delation mutant thus obtained showed a specific gravity of 1.465 which is somewhat smaller than that of 1.493 of its parent strain $\lambda cI857$ and a deletion in DNA of about 23%, as calculated from the specific gravity. In DNA of the parent phage $\lambda cI857$, the number of cleavages caused by the restriction enzyme Eco RI (supplied by Seikagaku Kogyo Co.) was five, whereas the number was three in the phage strain $\lambda cI857b6042$, as calculated from the number of survival determined by using $E.$ $coli$ W 3110 and $E.$ $coli$ W 3110 (RI).

$Esherichia$ $coli$ W 3110 (RI) was isolated in the following manner. A mixture of $E.$ $coli$ RY-13 (supplied by H. B. Boyer of the University of California) having a drug-resistance factor RI (resistant to penicillin, streptomycin, tetracyclin and sulfamides) and $E.$ $coli$ W 3110 (ATCC 27325) was culauted and $E.$ $coli$ W 3110 (RI) having drug-resistance factor was isolated.

2. Isolation of the phage strain $\lambda cI857b6042$ $RI^r$ absolutely resistant to the restriction enzyme Eco RI from the phage strain $\lambda cI857b6042$.

2-1. 0.25 ml of the overnight culture of $E.$ $coli$ W 3110 obtained as in 1-2 and 0.1 ml of the phage $\lambda cI857b6042$ suspension was mixed in 3 ml of molten $B_1$-soft agar held at 46° C. The resulting mixture was spread on a Tryptone-agar plate and cultured at 37° C. for 4 to 4.5 hours. To the plate were then added 4 ml of Tris-Mg buffer solution and 3 drops of chloroform. The plate was left standing at 37° C. for 15 minutes and the supernatant was transferred to a rubber-stoppered small test tube, the number of phage particles of the supernatant was $6 \times 10^{10}$/ml.

2-2. The number of particles of the phage obtained in 2-1 was measured by using E. coli W 3110 (RI) containing the restriction enzyme Eco RI. [E. coli w 3110 (RI) cleaves and inactivates the phage DNA intruded into its cell. Consequently, the number of phage particles measured by using E. coli W 3110 (RI) is far smaller than that measured by using E. coli W 3110 having no restriction enzyme. The former number was $10^8$/ml which is 1/600 of the latter number.]

In the same manner as in 2-1, a phage suspension was prepared by using 0.25 ml of the overnight culture of E. coli W 3110 (RI) obtained by culturing as described in 1-2 and 0.1 ml of a phage suspension obtained by diluting the phage prepared in 2-1 with Tris-Mg buffer solution to a phage particle concentration of $10^7$/ml, as measured by using the strain W 3110 (RI).

2-3. The phage obtained in 2-2 was treated by using the procedure described in 2-1. In this way, the treatment was repeated ten times by using alternately the procedures of 2-1 and 2-2. The final treatment was carried out by using the procedure of 2-1. A sample of the finally obtained phage suspension showed substantially the same number of phage particles as measured by using either the strain W 3110 (RI) or the stain W 3110, indicating that the phage suspension consisted of a mutant strain absolutely resistant to Eco RI. This phage suspension was diluted to $10^3$/ml and 0.1 ml of the diluted suspension was mixed with 0.25 ml of the culture of the strain W 3110. The resulting mixture was spread with molten $B_1$-soft agar on the Tryptone-agar plate to form plaques not overlapping one another. From the plaques thus formed, a phage strain $\lambda cI857b6042RI^r$ absolutely resistant to Eco RI was isolated.

3. Recombination between phage $\lambda cI857b6042$ $RI^r$ and phage $\phi 80$.

DNA of the phage $\lambda cI857$ lacks by nature Eco RI cleavage sites in the region carrying the genetic information for the production of coat proteins. In order to impart a cleavage sites to the said region, the Eco RI-resistant phage $\lambda cI857b6042$ $RI^r$ was crossed with the phage $\phi 80$, which is analogous to $\lambda$phage, and a new phage $\lambda cI857RI^r h80$ was obtained in the following way.

One platinum-loopful of E. coli W 3110 was inoculated into 1 ml of Tryptone medium and cultured by shaking at 37° C. for 16 hours. A 0.1 ml portion of the culture was added to 15 ml of Tryptone medium and cultured by shaking at 37° C. until the number of cells had reached $3 \times 10^8$/ml, and then the culture was centrifuged at 10,000 rpm for 10 minutes to collect the cells. The cells were suspended in 5 ml of Tris-Mg buffer solution and shaken for one hour at 37° C. 0.2 milliliter of the suspension was withdrawn into a test tube.

E. coli W 3110 was cultured in Tryptone medium by shaking at 37° C. for 3 hours, then infected by $\lambda cI857b6042RI^r$ and cultured for further 4 hours. The lysate was then diluted 30-fold with Tris-Mg buffer solution to obtain $\lambda cI857b6042RI^r$ suspension.

One platinum-loopful coliform bacillus (E. coli) K12 strain W 3110 ($\phi 80$) (ATCC 31277) was inoculated into 3 ml of Tryptone medium and precultured at 37° C. for 16 hours. The 3 ml preculture was added in 30 ml of Tryptone medium and cultured by shaking at 37° C. for 3 hours. A 15 ml portion of the culture was placed in a Petri dish, 15 cm in diameter, and irradiated with 15 W ultraviolet lamp at a distance of 50 cm for 1 to 2 minutes and thereafter again cultured by shaking at 37° C. for 4 hours. The resulting lysate was diluted with Tris-Mg buffer solution 30-fold to obtain $\phi 80$ suspension.

0.2 milliliter of the above $\lambda cI857b6042RI^r$ suspension ($3.4 \times 10^9$/ml) and 0.2 ml of the above $\phi 80$ suspension ($3.2 \times 10^9$/ml) were added to a 0.2 ml suspension of E. coli W 3110 preserved in the test tube and the mixture was incubated at 37° C. for 10 minutes. Thereafter, 0.1 ml of the mixture was added to 10 ml of Tryptone medium and shaken for 70 minutes at 37° C. Then, the culture was added by 7 drops of chloroform and shaken vigorously. 0.1 milliliter of the resulting mixture was mixed with E. coli W 3110 ($\phi 80$)/$\lambda$($\lambda$-resistant E. coli lysogenized with $\phi 80$). 3 milliliters of molten $B_1$-soft agar held at 46° C. was added to the above mixture and spread on a Tryptone-agar plate which was thereafter left standing overnight at 37° C. Phage particles were picked up by means of a bamboo spit from one of the plaques, and suspended in Tris-Mg buffer solution. Purification by plaque formation on E. coli W 3110 ($\phi 80$)/$\lambda$ was further repeated twice and a novel phage $\lambda cI85$-$7RI^r h80$ was obtained.

The above-noted E. coli W 3110 ($\phi 80$)/$\lambda$ was obtained in the following manner.

One platinum-loopful E. coli K12 strain W 3110 ($\phi 80$) (ATCC 31277) was inoculated into 2 ml of Tryptone medium and cultured at 37° C. for 16 hours. A mixture composed of 0.1 ml of the culture and 0.1 ml of $\lambda v$ phage suspension (IFO 20017) was kept at 37° C. for 30 minutes. After adding 3 ml of molten $B_1$-soft agar held at 46° C., the mixture was spread on a Tryptone-agar plate and cultured at 37° C. for 48 hours. By using a bamboo spit, the bacteria were picked out from one of the colonies on the plate and suspended in 5 ml of a sterilized 0.9% sodium chloride solution. 0.05 milliliter of this suspension was diluted 10,000-fold with sterilized 0.9% sodium chloride solution. 0.1 milliliter of the diluted solution was spread on a Tryptone-agar plate and cultured at 37° C. for 48 hours. The bacteria were picked out from one of the colonies formed on the plate and were used as W 3110 ($\phi 80$)/$\lambda$.

Note
(1) Tryptone-agar plate:
  1% of Tryptone (Difco); 0.25% of sodium chloride; 1.2% of agar; after sterilization by autoclaving 30 ml dispensed into each Petri dish, 9 cm in diameter.
(2) $B_1$-soft agar:
  1% of Tryptone (Difco); 0.25% of sodium chloride; 5 mM magnesium chloride; 1.5 $\mu$g/ml of vitamine $B_1$; 0.5% of agar; 3 ml was dispensed into each small test tube and sterilized by autoclaving.
(3) Tryptone medium:
  1% of Tryptone (Difco); 0.25% of sodium chloride The novel phage $\lambda cI875RI^r h80$ obtained as described above showed the following properties:

Host: The novel phage cannot infect $\phi 80$-resistant E. coli but $\lambda$-resistant ones. Host range is the same as that of phage $\phi 80$ and different from that of phage $\lambda$, indicating that at least a part of the coat proteins of the novel phage is the same as that of the phage $\phi 80$.

Immunity: Immunity is the same as that of phage $\lambda$.

Restriction by Eco RI: The novel phage showed a value intermediate between those of both parents.

Temperature sensitivity: The novel phage cannot produce active phage particles at 43° C. This coincides with the fact that synthesis of the coat proteins of phage φ80 is impossible at 43° C., as contrasted to the case of phage λ.

Production of the novel phage from lysogen: *E. coli* W 3110 was cultured in Tryptone medium by shaking at 37° C. for 24 hours. 0.25 milliliter of the culture ($4 \times 10^9$/ml) was mixed with 0.1 ml of a λcI857RI'h80 suspension ($10^3$/ml) and then with 3 ml of molten B$_1$-soft agar held at 46° C. The resulting mixture was spread on a Tryptone-agar plate and cultured overnight at 30° C. One platinum-loopful of lysogenized cells collected from one of the resulting turbid plaques were streaked on another Tryptone-agar plate and cultured overnight at 30° C. The cells collected from one of the developed colonies were those lysogenized with λcI857RI'h80. After having been cultured in Tryptone medium by shaking at 33° C. for 2 hours, this strain W 3110 lysogenized with λcI857RI'h80 was kept at 43° C. for 20 minutes to "induce" λcI857RI'h80 multiplication. Thereafter, the cultivation was again continued for 5 hours at 33° C. to obtain $3 \times 10^{11}$/ml of the phage λcI857RI'h80. The yield corresponded to 3 times the yield obtained in similar manner by lysogenizing λcI857 in *E. coli* W 3110, then culturing the lysogen, inducing the phage multiplication, and again culturing to yield a lysate.

Transduction: The novel phage can transduce the biosynthetic activity of tryptophan but not transduce the activity of galactose utilization.

From the above properties, it is apparent that in the phage λcI857RI'h80 the DNA region carrying the genetic information controlling self-replication of DNA has been derived from the phage λ and the DNA region carrying the genetic information concerning production of coat proteins has been derived from the phage φ80.

The phage λcI857RI'h80 obtained according to this invention has been deposited in the American Type Culture Collection (ATCC) and assigned the ATCC number 31285.

What is claimed is:

1. A temperate-bacteriophage whose DNA molecule is endonuclease-sensitive only in the DNA region carrying genetic information for the production of coat proteins.

2. A temperate-bacteriophage according to claim 1, wherein the temperate phage is a lambdoid phage.

3. A temperate-bacteriophage according to claim 2, wherein the lambdoid phage is λ(IFO 20016), 434(IFO 20018), 82(IFO 20019), φ80(IFO 20020), or φ170(IFO 20021).

4. A temperate-bacteriophage according to any of claims 1 to 2, wherein the endonuclease is a restriction enzyme.

5. A temperate-bacteriophage according to claim 4, wherein the restriction enzyme is Eco RI, Bam HI or Hind III.

6. Bacteriophage λcI857RI'h80 (ATCC 31285).

7. A culture of *E. coli* K12 strain lysogenized with the bacteriophage whose DNA molecule is endonuclease-sensitive only in the DNA region carrying genetic information for the production of coat proteins.

8. A cultue of *E. coli* K12 strain lysogenized with the bacteriophage λcI857RI'h80 (ATCC 31285).

9. A method for preparing a novel bacteriophage, which comprises making a bacteriophage of the lambdoid phage species endonuclease-resistant and mating the resulting bacteriophage with a lambdoid phage having endonuclease-sensitivity in the DNA region carrying genetic information for the production of coat proteins to obtain a bacteriophage having endonuclease-sensitivity only in the DNA region carrying genetic information for the production of coat proteins.

10. A method according to claim 9, wherein the bacteriophage of the lambdoid phage species is λ(IFO 20016), 434(IFO 20018), 82(IFO 20019), φ80(IFO 20020) or φ170(IFO 20021).

11. A method according to any one of claims 9 and 10, wherein the endonuclease is a restriction enzyme.

12. A method according to claim 11, wherein the restriction enzyme is Eco RI, Bam HI, or Hind III.

13. A method according to claim 9, wherein the endonuclease-resistant bacteriophage of the lambdoid phage species is made by microbial concentration technique.

14. A method according to claim 9, wherein the endonuclease-resistant bacteriophage of the lambdoid phage species is made by locally deleting the region of DNA cleavable by the restriction enzyme and then using the microbial concentration technique.

15. A method according to claim 14, wherein the local deletion of the region of DNA cleavable by the restriction enzyme consists in isolating a deletion mutant in which the phage DNA region including the cleavage sites has been deleted.

16. A method according to claim 9, wherein the mating is carried out by allowing a phage resistant to the restriction enzyme and a phage sensitive to the restriction enzyme successively or simultaneously to infect a *Escherichia coli* sensitive to both phages.

17. A method according to claim 9, wherein the prepared novel phage is isolated by growing the novel phage in the *E. coli* strain which can not adsorb the endonuclease-resistant bacteriophage and in which the endonuclease-sensitive phage is lysogenized.

* * * * *